United States Patent [19]

Bushong et al.

[11] Patent Number: 4,742,719
[45] Date of Patent: May 10, 1988

[54] MIXING PROCESS SIMULATING METHOD AND SYSTEM FOR EVALUATING WEDGE FLOW

[75] Inventors: David C. Bushong, Vassar; Bernard A. Loomans, Saginaw, both of Mich.

[73] Assignee: Baker Perkins, Inc., Saginaw, Mich.

[21] Appl. No.: 14,678

[22] Filed: Feb. 13, 1987

[51] Int. Cl.[4] .......................................... G01M 19/00
[52] U.S. Cl. ................................ 73/865.9; 73/862.26
[58] Field of Search ................ 73/865.6, 865.9, 862.26

[56] References Cited

U.S. PATENT DOCUMENTS 3,195,868  7/1965  Loomans et al. ...................... 366/85

*Primary Examiner*—Tom Noland
*Attorney, Agent, or Firm*—Learman & McCulloch

[57] ABSTRACT

A process simulator system for analyzing the forces imposed upon a mixing paddle of a predesignated configuration utilizes a rotary container with a curvilinear interior wall surface. A shaft extends into the container from above and supports a mixer paddle having a profile surface comprising side flanks of curvilinear configuration converging to an end surface concentric with the axis of the container which is immersed in the material adjacent the container wall surface. An indicator system provided with a zero force indicator and reactive to torque or bending forces imposed by the viscous material indicates the force imposed.

13 Claims, 4 Drawing Sheets

MIXING PROCESS SIMULATING METHOD AND SYSTEM FOR EVALUATING WEDGE FLOW

BACKGROUND OF THE INVENTION

This invention relates to systems for simulating and evaluating the wedge flow characteristics of mixing paddles of differing predetermined configurations mixing differing viscous materials to determine ideal paddle configurations for a particular viscous material. More particularly the invention is concerned with the dynamic measurement and evaluation of the torque forces and bending moments applied to a mixing shaft via a paddle having a curvilinear profile surface arranged stationarily at a so-called dispersion angle relative to a rotating curvilinear barrel or container surface.

Heretofore, paddle shape has been determined in continuous mixers of the type disclosed in U.S. Pat. No. 3,195,868 to Loomans, for example, by trial and error in laboratory mixers which are small scale versions of the mixer to be built for a particular throughput of material. The paddle shapes available were frequently not the most efficient configuration for mixing a specific material.

In the mixing systems which are available in the marketplace for mixing, blending and reacting materials in a continuous manner, the most efficient, for a wide variety of materials, are those of the co-generative type described in the aforementioned U.S. patent, wherein the mixer paddles are revolved in radially co-wiping relationship on twin mixer shafts which rotate at the same speed and in the same direction in a figure eight-shaped, stationary barrel chamber.

We have determined that the forces which are generated within such mixers are also generated when the paddle is maintained in a given stationary position within a revolving cylindrical bowl containing the viscous material.

SUMMARY OF THE INVENTION

One of the prime objects of the present invention is to provide a method and system for determining the optimum paddle configuration in terms of the power required to revolve the mixer paddle, while still providing optimum mixing and blending characteristics for the particular materials which are to be mixed.

A further object of the invention is to simulate the mixing process for the materials to be mixed and obtain force measurements which will enable the determination of the ideal paddle profile configuration for the mixing operation to be performed, the horsepower and speed of rotation required to achieve the mixing result, the proper sizes of the barrel chamber and paddle, and the number of pairs of radially inter-engaging, self-wiping paddles required to achieve a desired mixing result for a particular viscous material considering the variant parameters.

Still another object of the invention is to provide a simulating system and method which permits visual observation of the dispersion characteristics of one material in another in a manner which is reflective of the dispersion occurring in the mixer with a particular shape of paddle.

Still another object of the invention is to provide the mixing system simulator which, permits simultaneous measurement of the torque and bending forces applied to the paddle mounting shaft by the viscous liquid wedging between the paddle profile and barrel chamber.

Still another object of the invention is to provide a simulating system which permits the ready determination of the bending and torsion forces applied in a mixing system utilizing balance beam configurations which permit the simultaneous determination of the torque and bending forces applied during a simulated mixing process so that the two forces may be graphically compared or charted vis-a-vis changes in other parameters such as velocity.

A further object of the invention is to provide a simulating system which permits the analysis of the dynamic forces generated with particular paddle shapes, particular materials to be mixed, when surface finishes are varied, when the clearance or wiping spaces between the surfaces are varied, when the width of the paddles is varied, and when the material advancing angle of the paddle or screw segment mixing element is varied.

Another object of the invention is to provide a system of the character described which permits filming of the mixing operation for the purpose of recording and analyzing pressure distributions, flow paths, relative motions, and dispersion characteristics along the paddle flank profile as well as end effects at the edge of the profile.

Another object of the invention is to provide a system of the character described which can utilize and evaluate results when axially adjacent paddles of differing profile are provided at a given angular displacement one from the other.

Still another object of the invention is to provide a system and method for determining and observing the shear forces applied to the differing materials by paddle configurations which can differ widely. Other objects and advantages of the invention will be pointed out specifically or will become apparent from the following description when it is considered in conjunction with the appended claims and the accompanying drawings.

IN THE DRAWINGS

Figure 1:
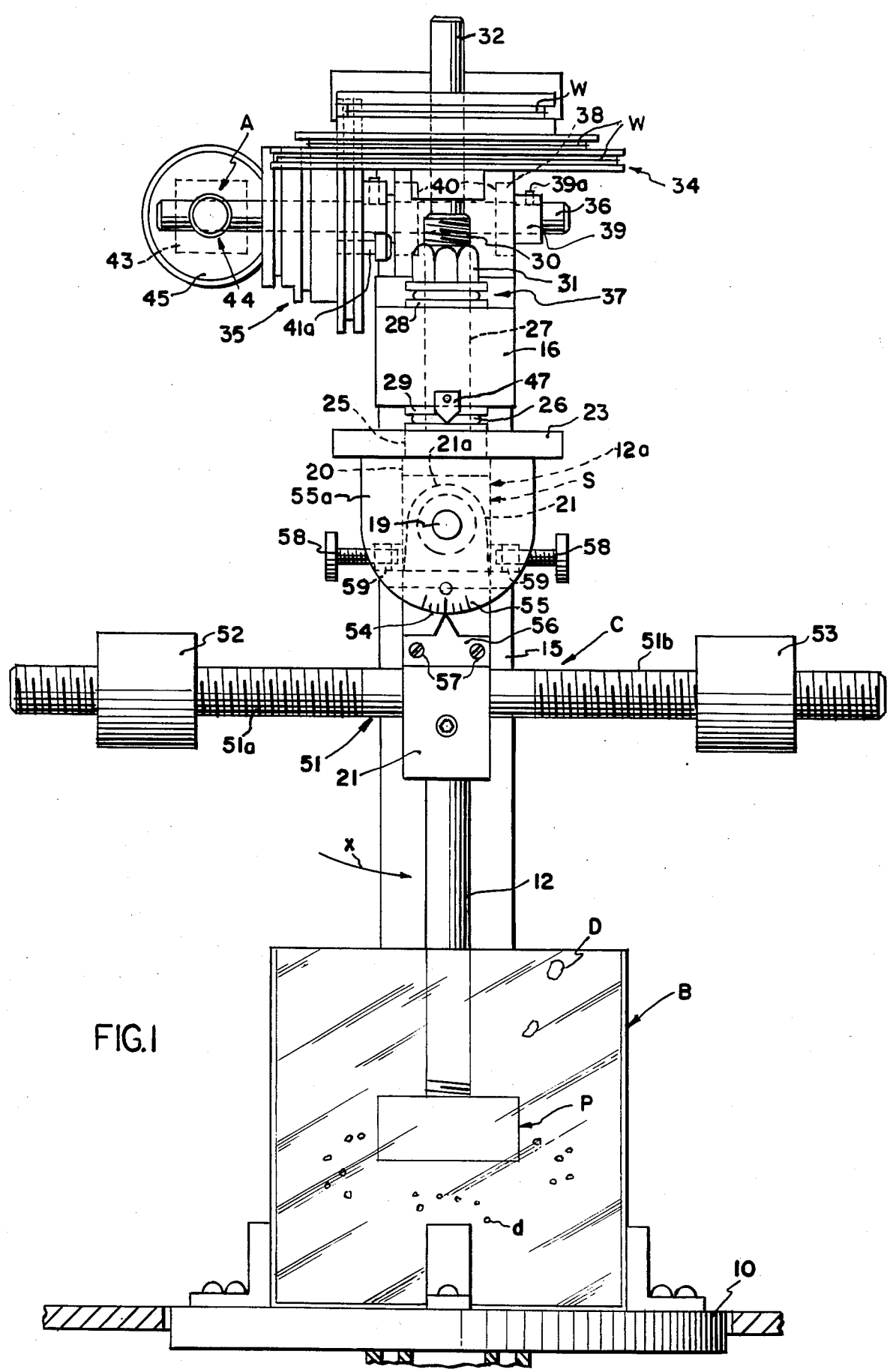
FIG. 1 is a front, elevational view, disclosing a single land mixing paddle, immersed in a bowl containing the test material, and connected with the system for measuring the bending forces generated.

Referring now more particularly to the accompanying drawings, and in the first instance to FIGS. 1-4, a letter B generally designates a bowl which is fixed to a turntable 10 driven by a suitable electric motor at a predetermined variable speed of rotation. Preferably, the motor is a reversible, variable speed motor, driving the turntable 10 and bowl B via a speed reduction system to provide the flexibility which is desired.

Immersed within the viscous material contained in bowl B, and extending below the level 11 of the liquid L therein, is a lower shaft element generally designated 12, on the lower end of which a paddle, generally designated P, is releasably fixed in stationary position. As FIGS. 1-3 indicate, for the sake of simplicity, the paddle P being tested is shown as of single land configuration, and comprises a crest portion 13 and flank profiles 13a, angular to the inner cylindrical wall surface 14 of the bowl B.

The shaft element 12, with its paddle P, is supported by a frame, generally designated F, which includes an upright support column 15 (FIG. 2) and a support arm 16. Support arm 16 is mounted for vertical travel on an adjustment screw 17 which is supported for rotary movement by the cylindrical column 15. The shaft 17 is prevented from moving axially, and as a result, the support arm 16, which is prevented from revolving with respect to column 15, is moved vertically along shaft 17 when the adjusting handle 18 is manipulated.

Figure 2:
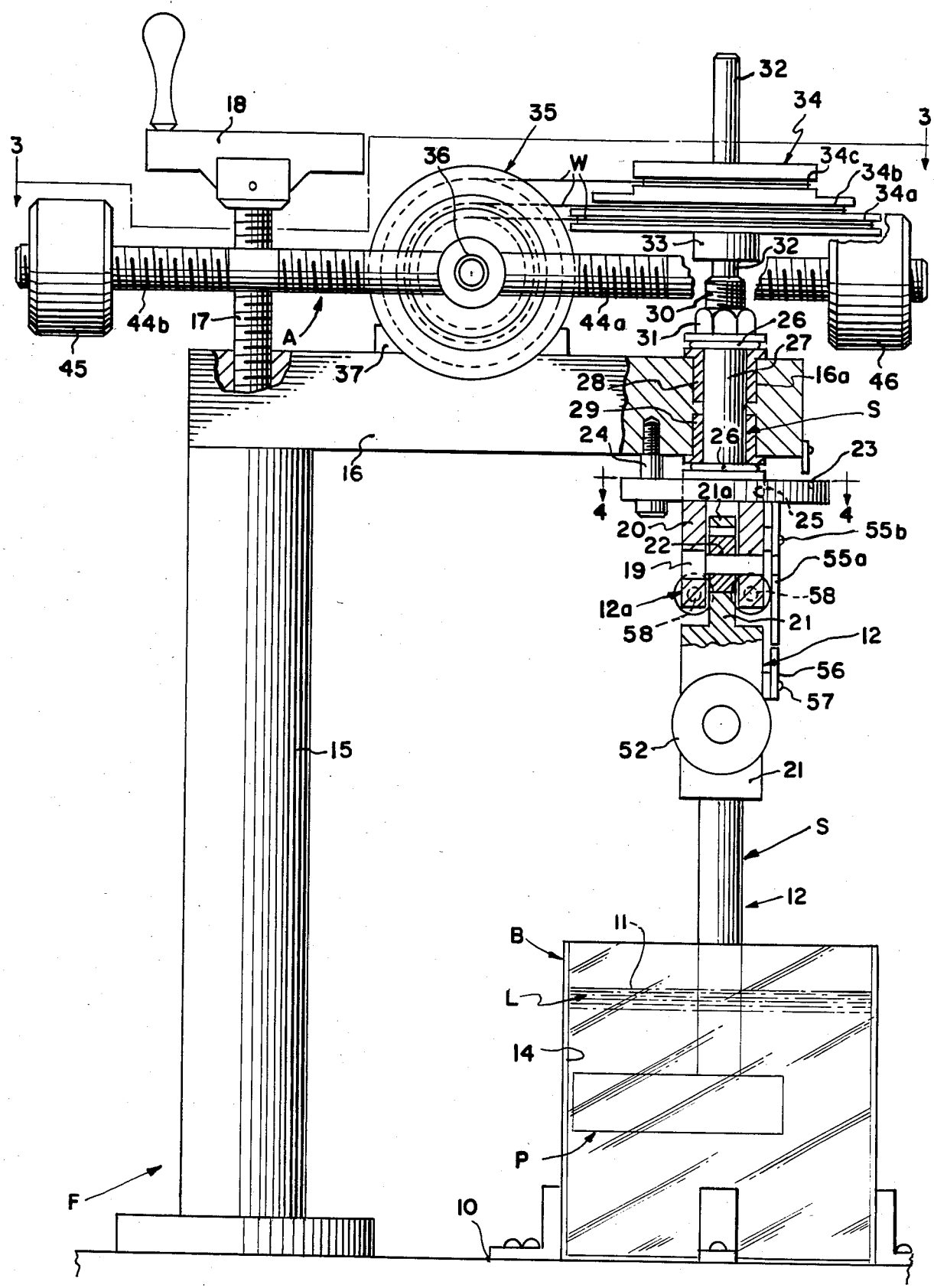
FIG. 2 is a side elevational view thereof, partly in section, and disclosing the manner in which applied torque forces are simultaneously measured.
Figure 3:
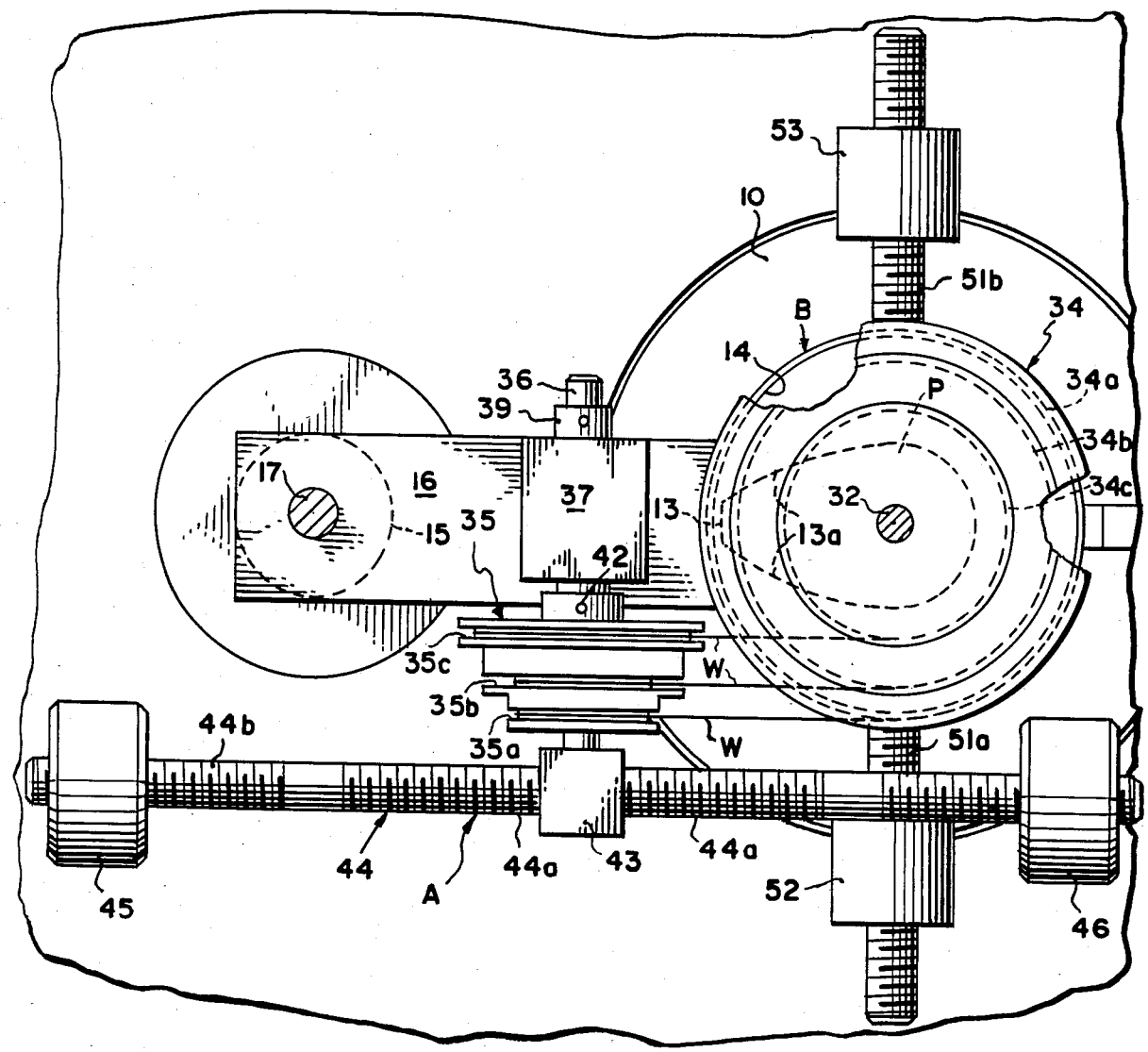
FIG. 3 is a fragmentary, top plan view, taken on the line 3—3 of FIG. 2.

The shaft part 12, as FIG. 2 particularly indicates, is part of a shaft assembly S, which includes the lower element 12, and an upper portion, generally designated 12a, which is pivotally connected to the lower portion by a pin 19, as disclosed in FIGS. 1 and 2. Upper shaft portion 12a includes clevis arms 20, for receiving the reduced width upper projection 21a of the shaft part 21, which supports the bearing 22, through which pin 19 extends. This construction permits the lower shaft portion 12 to be pivoted in an arc x (FIG. 1), about pivot pin 19 in a direction generally parallel to the portion of bowl wall 14, opposite the land or crest surface 13. Indicia bearing support plate 23, fixed to support arm 16, as with a machine screw 24, has an opening 25 through which clevis 20 extends. It will be seen that clevis 20, which is free to twist within opening 25, has an integrated shaft section 27, journaled by bearings 28 and 29, carried within a bore 16a in support arm 16.

The upper end of shaft section 27 is threaded as at 30 so that a nut 31 may be threaded down on the shaft section 30 to secure the rotary bearings 28 and 29 in position axially between thrust bearings 26, without exerting any force tending to restrict the rotation of clevis 20. The upwardly projecting portion 32 of threaded shaft section 30 mounts a pulley system, generally designated 34. The hub 33 of the pulley system 34 may be rigidly fixed to the shaft 32 by a suitable key or set screw (not shown). As FIGS. 1 and 2 indicate, the pulley system 34 has recessed annular tracks 34a, 34b and 34c of different diameter which are positioned to be adjacent and respectively level with the recessed, annular tracks 35a, 35b, and 35c respectively of a pulley system, generally designated 35, which is disposed at right angles to the pulley system 34. The smaller diameter track 35a of pulley system 35 is preferably opposite the larger diameter track 34a of the pulley system 34, and the larger diameter track 35c of the pulley system 35 is opposite the smaller diameter track 34c of the pulley system 34, for a purpose to be described.

The pulley system 35 is fixed to a shaft 36 which is freely journaled for rotation in a bearing block assembly, generally designated 37, mounted on arm 16. Bearings 38 are provided in bearing openings 40 provided in the bearing block assembly 37 to journal shaft 36 which is retained in position by a collar 39 secured by a set screw 39a. The hub 41 of the pulley system 35, which is fixed to the pulley system 35 by a screw 41a, is secured or keyed by set screw 42 to shaft 36, as shown in FIG. 1.

Each of the annular tracks 34a, 34b and 34c carry a flexible member, such as a longitudinally inextensible wire W, which has one of its ends fixed to the respective track of the pulley system 34 around which it winds, and its opposite end fixed to the adjacent track of the pulley system 35 around which it winds. In this way, the torsional rotation or twisting of the shaft assembly S is translated by the pulley systems 34 and 35, to rotation of the shaft 36 relative to fixed bearing block assembly 37.

Figure 4:
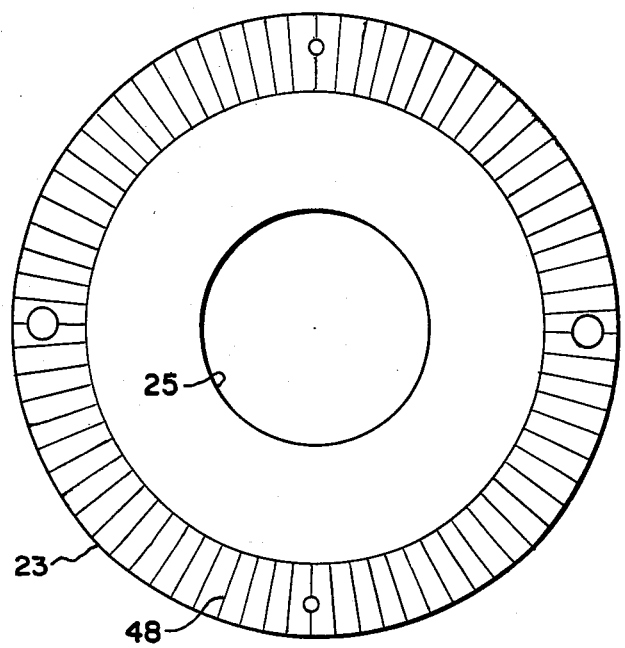
FIG. 4 is a transverse, sectional view taken on the line 4—4 of FIG. 2.

The outer end of shaft 36 rigidly mounts a balance beam assembly, generally designated A, which includes a nut 43, which adjustably receives a threaded shaft, generally designated 44. It will be seen that the shaft 44 has a centrally threaded section 44a, and a pair of threaded sections 44b and 44c, which are of opposite hand. The threaded section 44a permits absolute centering of the shaft 44 relative to nut 43. Mounted on the end threaded sections 44b and 44c are a pair of identical counter-weights 45 and 46 which may be axially adjusted along the shaft 44 by simply rotating them. An indicator pointer 47 is carried on arm 16 in stationary position, as shown. When the balance beam assembly, generally designated A is properly adjusted, pointer 47 will be opposite the zero position on the scale 48 provided on the upper face of plate 23, as shown in FIG. 4. When the balance beam assembly A is in balance and the bowl B is not rotating, the indicator 47 will be in this neutral position in which no torsion is being applied to shaft assembly S.

A similar balance beam assembly, generally designated C, is provided to measure the bending forces which are applied to the shaft section 12. This balance beam assembly C includes the part 21, fixed to the shaft section 12, which fixedly mounts generally horizontal shafts, generally designated 51, having threads 51a and 51b of opposite hand on their ends. Identical counter-weights 52 and 53 are adjustably threaded on the threaded ends 51a and 51b respectively, and can be adjusted axially thereon to place the lower shaft section 12 in a position of equilibrium with reference to a zero reference indicia 54 provided on a scale 55, carried on scale plate 55a, fixed as by screws 55b to one of the clevis arms 20. An indicator plate 56 is carried by shaft part 21, as by means of screws 57. Adjusting screws 58 are threadedly received by nuts 59, fixedly secured by the clevis arms 20 and operate as stops to limit the tilt of the balance beam C.

Figure 5:
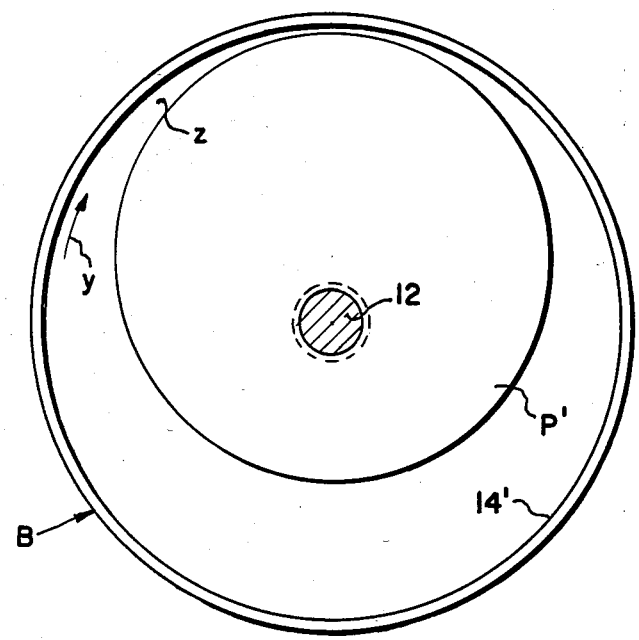
FIG. 5 is a top plan view, showing a different configuration of mixer paddle immersed in the viscous liquid contained in the bowl chamber.

In FIG. 5, an alternate form of paddle P' is disclosed on the shaft part 12. As indicated the paddle is a circular disc which is mounted eccentrically on the shaft element 12 in a stationary position relative to the rotating bowl wall 14' which moves in the clockwise direction indicated by the arrow y. In this version of the invention, the material L tends to be wedged against the profile of the paddle in the area z and exerts a pressure thereagainst, tending to twist the shaft S, as well as bend it.

THE OPERATION

Referring particularly to FIGS. 1-4, and assuming it is desired to test the configuration of the single land paddle P as a mixing paddle for a viscous plastic, for example, such as a polymer like polybutane. The first step is to adjust the balance beam structures A and C to the balanced "zero" position. This is accomplished by adjusting the positions of the counter-weights 45 and 46 to an equidistant position from the axis of pin 19. It will be known from previous experimentation about what moment arm is involved for a material of similar viscosity from the axis of shaft 36, insofar as the one weight 46 is concerned, and the other weight 45 is then adjusted to provide a balanced condition in which the indicator 47 is at the zero position on the scale on disc 23. The counter-weights 52 and 53 are then adjusted similarly to provide the "zero" balance condition in which indicator 56 is at the "zero" reference position shown in FIG. 1. The adjustable stop screws 58 may be adjusted to limit the tilt of shaft 51 so that it does not move too far.

When the turntable 10 and bowl B are then rotated at a predetermined speed, the bending forces imposed by the viscous fluid L upon shaft S via the paddle P, tend to bend the lower part 12 of shaft S about pin 19 to a given position. The degree of force may be observed on scale 55, unless the force is of such amplitude that one of the adjustable stops 58 limits the tilt. The one counter-weight 52 can then be adjusted to again restore the pointer 56 to the zero position and, via measurement with a rule, the change in moment arm can be determined. This change in moment arm multiplied by the weight of counter-weight 52 will, of course, be a measurement of the bending force involved. This bending force can then be compared with the bending force imposed upon paddles of differing shape, or bowls rotating at differing speeds. Alternately, the counter-weights can be adjusted in opposite directions to achieve a condition of rebalance when the forces imposed are large, and the changes in moment arms measured.

At the same time bending forces are imposed on shaft S, torque forces tending to twist the shaft S are also imposed by the wedging effect of the liquid L, and this is reflected by the pivoted condition of balance beam screw shaft 44. Again the degree of force is visually indicated upon the scale shown in FIG. 4. Again an adjustment of one of the counter-weights 45 to restore the beam 44 to the balanced condition in which indicator pointer 47 indicates the "zero" position, and measurement of the change in moment arm will determine the torque involved for the particular paddle shape vis-a-vis the particular material. Obviously, again this measurement may be compared with a like measurement obtained for a differently shaped paddle. It is often very useful to simultaneously plot the bending and torque forces on the same chart for the same paddle profile when bowl B is moved at different velocities.

Other testing can involve different paddle thicknesses, different paddle surface finishes, and various variations in paddle configurations such as flank length and flank curvature. The forces in torsion and bending which are exerted, can be compared with the torsion and bending forces imposed upon the paddle P' shown in FIG. 5, or other paddle shapes. The forces generated upon the lenticular paddles, disclosed in the aforementioned Loomans U.S. patent may also be measured since they mirror the position of rotation of a lenticular paddle in a figure-8 shaped barrel, when both crests or land ends are directly adjacent a section of the barrel wall. In this condition of the paddles, the torsional forces exerted upon the shaft tend to double, while the bending forces tend to cancel one another.

Since bowl B is transparent, the rate of dispersion may be determined, using a suitable stop-watch, for example. If ¼ inch diameter droplets D of pigment are added to the viscous liquid, the observer can record the length of time which elapses before the droplets D sub-divide to ten millimeter diameter globules d. This observation is a measurement of the shear rate with the paddle profile which is being tested. The shear rate is a parameter which is reflected by the so-called drag effect occurring because there is relative travel between the bowl and the paddle, and the degree of wedge flow. The severity of the approach curvature of the flank to the land end, affects wedge flow characteristics as does the length of the crest or land, and the wiping clearance between the crest or land and the container wall. With the process and system described, ideal parameters can be extrapolated for a different material being mixed to achieve optimum paddle configurations which balance various factors involved for most efficient and thorough mixing. The full-size mixer which results, then achieves good uniform mixing without wasting energy and requiring undue mixer horsepower.

It is, of course, possible to heat the bowl B so that initially a solid material can be disposed in the bowl, and observations and measurements can occur over the melting range. Further devolatilization rates can be observed, by sealing the top of the bowl from atmosphere and observing the bubble formation. A wide variety of polymer and other viscous materials, of the character mentioned in the patents to which reference has been made, can be employed in the testing procedures, dependent on the mixing or blending process which is to be achieved.

While one embodiment of the invention has been described in detail, it will be apparent to those skilled in the art that the dislosed embodiment may be modified. Therefore, the foregoing description in all aspects is to be considered exemplary rather than limiting in any way, and the true scope of the invention is that defined in the following claims.

What is claimed is:

1. In a process simulator for analyzing the forces imposed upon a mixing paddle of a designated configuration, the combination of elements with frame means comprising:

a. a viscous liquid container having an interior wall surface;

b. a shaft supported by said frame means extending into said container;

c. a mixer paddle adapted to be secured rigidly on said shaft within said container and immersed in said liquid, said paddle having a profile surface, radially offset from said container wall surface, such that it lies adjacent the container wall surface at a wedge angle relative thereto, whose characteristics, for the liquid in the container, are to be determined;

d. means for rotating said container wall surface relative to said shaft and paddle;

e. first indicator means provided with a zero force indicator and reactive to torque forces imposed upon said shaft by the liquid dispersed between the said wall surface and the said paddle profile surface to indicate the torque imposed in terms of the zero force as a reference; and f. second indicator means provided with a zero force indicator and reactive to bending moment applied to said shaft by the said liquid between the said wall surface and the said paddle profile surface to indicate the bending moment imposed in terms of the zero force reference.

2. The invention of claim 1 wherein said second indicator means comprises a weight bearing balance beam disposed crosswise to said shaft and rigidly connected thereto; said shaft is supported for pivotal movement about an axis perpendicular to a central axis thereof; a pointer is provided on the beam; and a scale having a zero reference is supported independently so that the pointer on said shaft can indicate any pivot of the shaft under bending force with said scale.

3. The invention of claim 2 in which said balance beam is threaded at both of its ends and counter-weights having axial, threaded openings are received on the ends of said beam for adjustment thereon on opposite sides of the balance beam pivot.

4. The invention of claim 1 wherein said first indicator means comprises a weight bearing balance beam pivotally supported on said frame means crosswise to said shaft; a pulley system fixed to said balance beam with a central axis of the pulley system aligned with the pivot axis of the balance beam; a pulley system fixed to said shaft; and inextensible flexible elongate means connects said pulley systems to translate the torque forces imposed to twist said shaft to forces seeking to pivot said balance beam; there being pointer and scale means for indicating the movement of said shaft in torsion relative to a zero force reference.

5. The invention of claim 4 in which said balance beam is threaded at both of its ends and counter-weights having axial threaded openings are received therein for adjustment thereon on opposite sides of the balance beam pivot.

6. The invention of claim 1 in which said shaft comprises a first part and a second part, said first part being pivoted on said second part about an axis perpendicular to a central axis of said shaft; said first indicator means coacting with said first part and said second indicator means coacting with said second part.

7. The invention of claim 6 in which said paddle is fixed to said first shaft part and said second shaft part is journaled for rotation by said frame means.

8. The invention of claim 1 wherein said first and second indicator means each includes a centrally pivoted balance beam with weights on the ends thereof, movable along the ends thereof to impose predetermined counter-balancing forces on said shaft.

9. A process simulator system for analyzing the forces imposed upon a mixing paddle of a predesignated configuration, comprising:
   a. a container containing a material to be tested having a curvilinear interior wall surface;
   b. frame means;
   c. a shaft supported by said frame means, extending into said container from above;
   d. a mixer paddle releasably secured rigidly on said shaft to be immersed in the material in said container, said paddle having a profile surface comprising side flanks of curvilinear configuration converging to an end surface concentric with the axis of the container, and lying adjacent said container wall surface;
   e. means for rotating said container wall surface relative to said shaft and paddle;
   f. indicator means provided with a zero force indicator and reactive to one of the torque and bending forces imposed upon said shaft by the viscous material disposed between the said container wall surface and the said paddle profile surfaces to indicate the force imposed in terms of a balance reference; and
   g. means restoring the indicator means to original position once the rotation of the container ceases.

10. The invention of claim 9 wherein said indicator means comprises a weight-bearing balance beam carried by said shaft and disposed crosswise to said shaft, and indicia is provided for determining the degree of force which is exerted upon the paddle.

11. A process simulating method for analyzing forces imposed upon a mixing paddle of a predesignated configuration utilizing a selectively rotated, viscous liquid container filled at least partly with a predesignated viscous liquid, and having an interior wall surface; a shaft suspended by frame means into the upper end of the container having the mixer paddle secured rigidly within the container in a state of immersion within the viscous liquid, the paddle having a profile surface including convergent curvilinear flanks joining to a crest or land surface concentric with the container wall surface with the land disposed adjacent radially to the container wall surface and the flank surface providing wedge flow with rotation of the container, and a mechanism provided with a zero force determinator and reactive to at least one of the torque and bending forces imposed upon the shaft by the liquid wedge flow between the container interior wall and the paddle to determine the forces imppsed in terms of the zero force as a reference comprising the steps of:
   a. adjusting the determinator to the zero force position;
   b. rotating the container relative to the paddle at a predetermined speed; and
   c. determining the force imposed upon the shaft via the paddle relative to a static zero force.

12. The method of claim 11 including the step of separately indicating the torque forces imposed upon the shaft and the bending forces imposed upon the shaft, each relative to a static zero force indication.

13. The method set forth in claim 12 wherein balance beam means is provided as a part of said determinator means, and comprises identical weights at each of its ends, at least one of which is adjustable whereon; the steps comprising: adjusting at least one of the weights along the balance beam on one side of the balance beam pivot to achieve a known position of balance at the zero force position; observing the extent to which the balance beam is thrown out of balance when forces are applied to the paddle; and measuring the change in moment arm required to again balance the beam during the time forces are being applied to the paddle.

* * * * *

UNITED STATES PATENT AND TRADEMARK OFFICE
CERTIFICATE OF CORRECTION

PATENT NO. : 4,742,719
DATED : May 10, 1988
INVENTOR(S) : David C. Bushong and Bernard A. Loomans It is certified that error appears in the above-identified patent and that said Letters Patent is hereby corrected as shown below:

Column 1, line 65, change "the", second occurrence, to -- a -- .

Column 8, line 33, change "imppsed" to -- imposed -- ;

line 48, change "whereon" to -- thereon -- .

Signed and Sealed this

Twentieth Day of September, 1988

Attest:

DONALD J. QUIGG

*Attesting Officer*         *Commissioner of Patents and Trademarks*